United States Patent
Nakamura et al.

(10) Patent No.: US 6,616,330 B2
(45) Date of Patent: Sep. 9, 2003

(54) AUTOMATIC HUMIDITY STEP CONTROL THERMAL ANALYSIS APPARATUS

(75) Inventors: Nobutaka Nakamura, Chiba (JP); Toshihiko Nakamura, Chiba (JP); Noriyuki Takata, Shizuoka (JP)

(73) Assignees: Seiko Instruments Inc. (JP); Chugai Seiyaku Kabushiki Kaisha (JP)

( * ) Notice: Subject to any disclaimer, the term of this patent is extended or adjusted under 35 U.S.C. 154(b) by 0 days.

(21) Appl. No.: 10/001,335

(22) Filed: Oct. 26, 2001

(65) Prior Publication Data

US 2002/0080848 A1 Jun. 27, 2002

(51) Int. Cl.<sup>7</sup> ......................... G01N 25/00; G01N 25/56
(52) U.S. Cl. ............................. 374/14; 374/11; 374/31; 73/865.6
(58) Field of Search ............................. 374/14, 11, 10, 374/31, 57, 45, 149; 73/865.6

(56) References Cited

U.S. PATENT DOCUMENTS

| | | | | |
|---|---|---|---|---|
| 3,045,472 A | * | 7/1962 | Paulik et al. | 374/10 |
| 3,344,654 A | * | 10/1967 | Erdey et al. | 374/14 |
| 3,916,670 A | * | 11/1975 | Davis et al. | 374/14 |
| 4,668,854 A | * | 5/1987 | Swan | 236/44 R |
| 5,013,159 A | * | 5/1991 | Nakamura et al. | 374/12 |
| 5,321,719 A | * | 6/1994 | Reed et al. | 374/14 |
| 5,669,554 A | * | 9/1997 | Nakamura et al. | 374/14 |

* cited by examiner

Primary Examiner—Diego Gutierrez
Assistant Examiner—Stanley J. Pruchnic, Jr.
(74) Attorney, Agent, or Firm—Adams & Wilks

(57) ABSTRACT

An automatic humidity step control thermal analysis apparatus has a detector for detecting and measuring a physical property of a sample and for generating a physical property signal corresponding to the physical property of the sample. The sample is housed in a sample chamber which is capable of controlling the temperature and humidity of the sample. A water chamber generates water vapor at a preselected temperature and is capable of controlling the temperature of water in the water chamber in a stepwise manner. A heat insulating pipe directs water vapor from the water chamber to the sample chamber and includes a heater for preventing dew condensation. A signal stability determination circuit receives a physical property signal from the detector and generates a trigger signal when a rate of change of the physical property signal drops below a preselected reference value. A control device controls the temperature of water in the water chamber in a stepwise manner in accordance with the trigger signal generated by the signal stability determination circuit to thereby adjust the humidity of the sample chamber in a stepwise manner.

20 Claims, 2 Drawing Sheets

AUTOMATIC HUMIDITY STEP CONTROL THERMAL ANALYSIS APPARATUS

BACKGROUND OF THE INVENTION

1. Field of the Invention

The present invention relates to a new improved thermal analysis apparatus for analyzing changes of physical properties of a sample as a function of temperature, wherein the effect of the humidity of the periphery of a sample on the physical properties of the sample can be evaluated.

2. Background Information

Thermal analysis is an effective means for investigating how the physical properties of a material change with temperature. Examples of thermal analyzers include Differential Thermal Analyzers (DTA), Differential Scanning Calorimeters (DSC), Thermogravimetric Analyzers (TG), Thermomechanical Analyzers (TMA), and Dynamic Mechanical Analyzers (DMA). An improved thermal analysis apparatus providing a humidity control function is disclosed in Japanese Patent Laid-open No. Tokkaihei 8-145918.

Furthermore, an automatic moisture absorption equilibrium measurement device comprised of a combined microbalance and humidification device is available on the market.

In the prior art thermal analysis apparatus with a humidity control function described in Patent Laid-open No. Tokkaihei 8-145918, the program control is performed not only for the temperature but also for the humidity in the periphery of the sample. The humidity scanning measurement enabled by performing program control for humidity provides a great advantage. On the other hand, compared to the case of temperature equilibrium, the time required for the physical property of the sample at a certain humidity to reach equilibrium is extraordinary long. There is the problem that evaluation of the humidity dependency of the physical property of the sample is inaccurate unless the humidity scanning speed is set very low. Moreover, since the time required for the sample to reach humidity equilibrium depends on the shape and physical and chemical properties of the sample, there is the problem that the humidity program cannot be built adequately without obtaining knowledge about the hygroscopicity of the sample in advance.

On the other hand, an automatic moisture absorption equilibrium measurement device obtains desired relative humidity by mixing dry nitrogen and saturated vapor at a certain ratio, and comprises a precision gas flow rate control device, a vapor generating device, a mixing device, a drainage device, and a microbalance. The disadvantages are that this prior art device is expensive because of its complicated construction and lacks versatility as it cannot be used with a thermal analysis apparatus.

To measure the sample absorbed moisture at a certain humidity and reach the equilibrium state with the thermal analysis apparatus of the related art, during sampling and introduction of the sample, the device is exposed to an atmosphere in which the humidity is not controlled. Therefore, there is a problem that the system deviates from the equilibrium state before the measurement starts.

SUMMARY OF THE INVENTION

To resolve the above problems, an automatic humidity step control thermal analysis apparatus according to the present invention has a water chamber capable of temperature step control for generating saturated vapor at an appropriate temperature, a sample chamber for housing a sample and capable of changing the temperature and humidity of the sample, a heat insulation pipe for directing vapor from the water chamber to the sample chamber while preventing dew condensation, a detector for detecting and measuring physical properties of the sample, an a signal stability determination circuit for generating a trigger signal in case that the rate of change of the physical property signal from the detector drops below a specified reference value. In this case, the humidity of the sample chamber is determined according to the ratio of the saturated vapor pressures at the temperature of the hot water chamber and at the temperature of the sample chamber. The water temperature of the hot water chamber is changed corresponding to the trigger signal in a stepwise manner and, accordingly, the humidity of the sample chamber is also changed in a stepwise manner. As a result, the humidity equilibrium of the sample and the atmosphere in the periphery of the sample is confirmed based on the physical property of the sample, and a humidity condition is then automatically scanned in a stepwise manner.

Furthermore, if the sample, which previously absorbed moisture at a certain humidity and reached the equilibrium state, is caused to deviate from its state of equilibrium temporarily, the signal stability determination circuit determines the change of the physical property signal by controlling the humidity of the sample chamber and confirms whether or not it returns to its state of equilibrium with the trigger signal at the measurement start.

DETAIL DESCRIPTION OF THE PREFERRED EMBODIMENT

Figure 1:
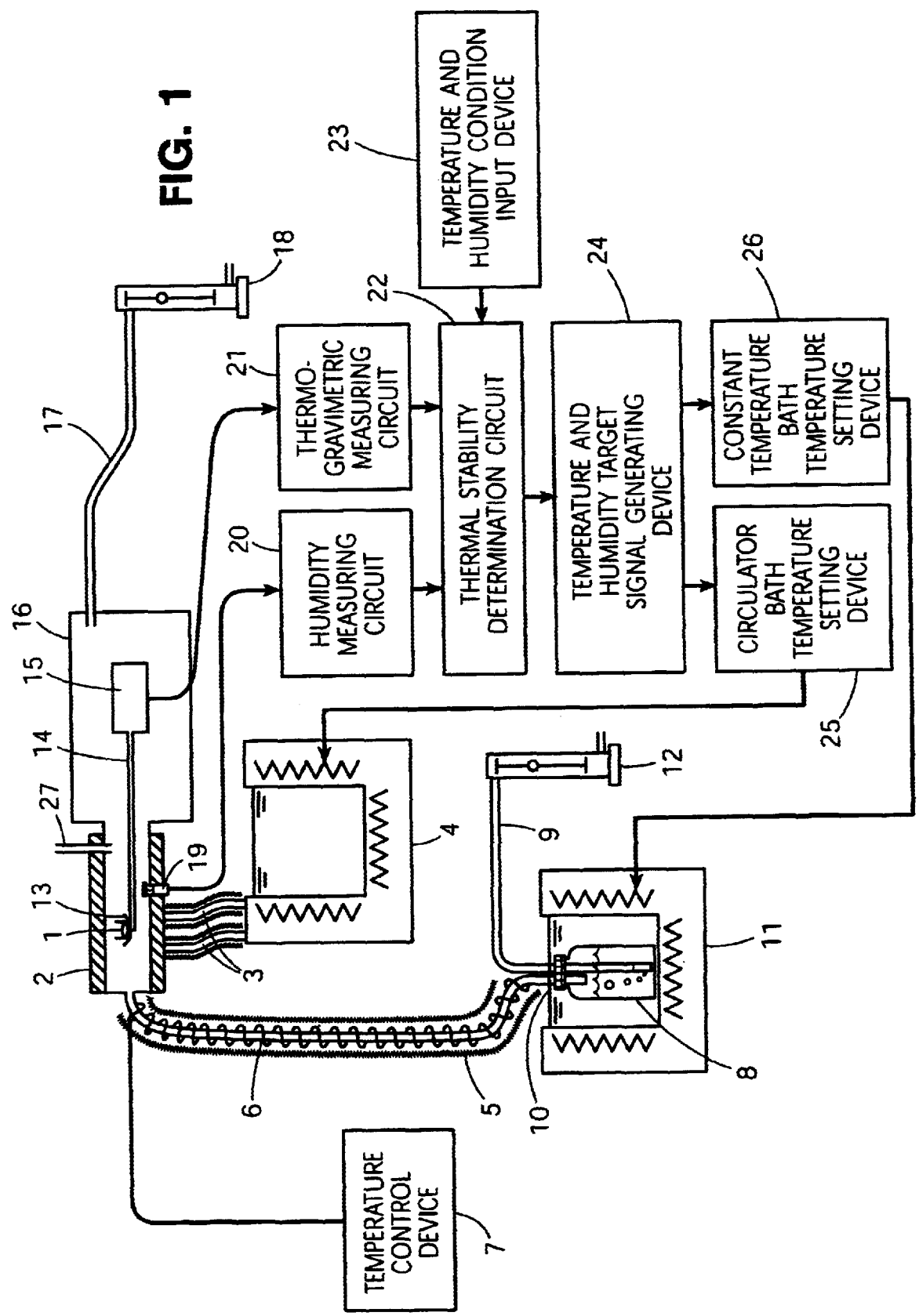
FIG. 1 is a block diagram with parts shown in partial cross-section of an automatic humidity step control thermal analysis apparatus according to an embodiment of the present invention.

An embodiment of the present invention will be described with reference to FIGS. 1–2. A device for thermogravimetry measurement with application of the present invention is described in FIG. 1. 1 in FIG. 1 is a sample to be measured. A heat retaining furnace 2 made of stainless steel with a cylindrical inside cavity is arranged to wrap around sample 1. One end of the heat retaining furnace 2 is sealed composing a bottom surface, and another end is open. A constant temperature circulator bath 4 capable of temperature setting is connected to the heat retaining furnace 2 via hose 3,3. A liquid medium, for example, water, in a constant temperature circulator bath 4, is circulated to and from the cavity within the heat retaining furnace 2 via hose 3 to make the temperature of the entire heat retaining furnace 2 close to the set temperature of the constant temperature circulator bath 4.

A heat insulation pipe 5 penetrates through the bottom surface of the heat retaining furnace 2. The other end of the heat insulation pipe 5 is introduced into the inside of a glass bottle 8. A heat insulation pipe temperature control device 7 is connected to a heater 6 embedded in the heat insulating pipe 5. The glass bottle 8 is filled with distilled water, approximately seven-tenths, and plugged with a rubber stopper 10, which is penetrated by a bubbling gas introduction pipe 9 and also by a TEFLON tube core constituting the heat insulating pipe 5. The glass bottle 8 is fixed in the water within a constant temperature bath 11, the temperature of which is capable of being preset, with almost the whole glass bottle submersed in the water, so that the temperature inside the glass bottle 8 is close to set temperature of the constant temperature bath 11. One end of the bubbling gas introduction pipe 9 is connected to a flow meter 12.

A sample container containing the sample 1 is mounted on a sample holder 13. Changes in weight and temperature of the sample 1 are measured at a balance unit 15 provided inside a balance case 16 after passing through a balance beam 14 with the thermocouple embedded. A flow meter 18 is connected to a part of the balance case 16 via a purge gas introduction tube 17. The thermogravimetry measurement device shown in FIG. 1 is of a horizontal type with the balance beam 14 provided in a horizontal manner. This also can be applied to the thermal gravity measurement device, for example, an above-balance type or a below-balance type measurement device.

The inner portion of the heat retaining furnace 2 is provided with a gas outlet 27 and with a humidity sensor 19. The humidity of the atmosphere in the periphery of the sample 1 is measured by a humidity measuring circuit 20 connected to the humidity sensor 19. On the other hand, changes of weight and temperature of the sample 1 are measured by a TG measuring circuit 21 connected to the balance unit 15. A signal or thermal stability determination circuit 22 is connected to the humidity measuring circuit 20 and the TG measuring circuit 21. A temperature and humidity condition input device 23 is connected to the thermal stability determination circuit 22. The thermal stability determination circuit 22 is also connected to a temperature and humidity target signal generating device 24. A circulator bath temperature setting device 25 and a constant temperature bath temperature setting device 26 are also connected to the temperature and humidity target signal generating device 24. The constant temperature circulator bath 4 is connected to the circulator bath temperature setting device 25, and the constant temperature bath 11 is connected to the constant temperature bath temperature setting device 26.

Next, the operation of the apparatus shown in FIG. 1 is described.

Prior to measurement, the operator sets the flow rate of purge gas at 200 ml/min with the flow meter 18 to protect the balance unit from dew condensation, then introduces the purge gas into the balance case 16 via the purge gas introduction tube 17. The flow rate of the flowmeter 12 is set at 200 ml/min, and dry air or nitrogen gas is allowed to flow. The air or nitrogen gas flowing from the flow meter 12 is transmitted into the glass bottle 8 via the bubbling gas introduction pipe 9 which is introduced in the vicinity of the bottom surface in the water within the glass bottle 8, and is introduced, as gas including the vapor at saturated vapor pressure corresponding to the water temperature, in the periphery of the sample 1 within the heat retaining furnace 2 via the heat insulation pipe 5. The open end of the heat retaining furnace 2 is in close contact with the balance case 16, and the purge gas and the saturated vapor are both exhausted to the outside via the gas outlet 27.

Next, the heat retaining furnace 2 is moved, and the sample 1 to be measured is placed in the container and then in the sample holder 13, and the heat retaining furnace 2 is replaced (the moving means for moving the heat retaining furnace is not shown). The temperature and humidity range over which measurements are to be performed, for example, a temperature of 50 degrees and a relative humidity of 30%–70%, are input at the temperature and humidity condition input device 23, and then measurement is started.

When the measurement is started, using the input signal of the temperature and humidity condition input device 23, the target signal of the temperature and humidity is immediately transmitted from the temperature and humidity target signal generating device 24 to the circulator bath temperature setting device 25 and the constant temperature bath temperature setting device 26. At the circulator bath temperature setting device 25, a temperature target signal is extracted and sent to the constant temperature circulator bath 4. At the constant temperature circulator bath 4, temperature control is started, setting its target value at the temperature signal from the circulator bath temperature setting device 25. As a result of thermal transmission caused by the water circulating inside, after a short time the temperature of the heat retaining furnace 2 connected to the constant temperature circulator bath 4 via the hose 3 will be equal to the temperature of the constant temperature circulator bath 4. Also, the temperature of the sample 1 gets close to the temperature of the heat retaining furnace 2. As a result, the temperature of the sample 1 gets close to the temperature of the constant temperature circulator bath 4, namely, the target temperature outputted from the circulator bath temperature setting device 25. The temperature of the sample 1 is detected by a thermocouple (not shown) welded on the bottom surface of the sample holder 13 and is converted into a measurement temperature signal at the TG measuring circuit 21 after being transmitted through the balance beam 14 and the balance system 15.

On the other hand, at the constant temperature bath temperature setting device 26, the target temperature of the constant temperature bath 11 is calculated as follows based on the target temperature and humidity condition.

That is, if the temperature of the constant temperature bath 11 is taken to be Tw, the temperature inside the glass bottle 8 will be Tw. If the saturated vapor pressure at the temperature T is taken to be P(T), the vapor pressure of the gas introduced in the periphery of the sample via the heat insulating pipe 5 is given by P(Tw). The temperature of the heat pipe 5 is kept higher than the temperature of the constant temperature bath 11 by the function of the temperature control device 7 and the heater 6. On the other hand, as previously noted, the temperature in the periphery of the sample 1 is approximately equal to the temperature of the constant temperature circulator bath 4. If this temperature is taken to be Td, the relative humidity RH produced by the atmosphere at the vapor pressure P(Tw) introduced in the periphery of the sample is expressed by the following equation (1):

$$RH(\%) = \{P(Tw)/P(Td)\} \times 100 \qquad (1)$$

Accordingly, to set the sample temperature at Td and the sample humidity at RH(%), the temperature Tw, the temperature for the constant temperature bath 11, is given by the following equation (2) after solving equation (1):

$$Tw = P{-}1[RH(\%) \times P(Td)/100 \qquad ] (2)$$

Here, P−1 is the inverse function of P, which converts the saturated vapor pressure into the corresponding temperature, namely, T=P−1[P(T)].

At the constant temperature bath temperature setting device 26, Tw is calculated based on equation (2), and the temperature of the constant temperature bath 11, that is, the temperature of the glass bottle 8, is controlled while setting Tw as its target.

At this point, the relative humidity in the periphery of the sample 1 is detected by the humidity sensor 19 periodically, and converted into the humidity signal at the humidity measuring circuit 20.

The weight of the sample 1 may change with the change in temperature or humidity. The change in weight of the sample is detected at the balance unit 15 after passing through the balance beam 14, and is converted into the thermogravimetry (TG) signal at the TG measuring circuit 21.

Signals corresponding to the temperature, TG, and the humidity measured at the TG measuring circuit 21 and at the humidity measuring circuit 20 are transmitted to the signal stability determination circuit 22, where the stability of each signal and the difference of the temperature and humidity signal from the target value is evaluated.

At the signal stability determination circuit 22, when temperature and humidity signals fulfill the standard condition for the preset rate of change, for example, 0.2 degrees per minute or under and 1% per minute or under, the difference between the measured value and the set target value of the temperature and humidity is evaluated. When the difference in temperature is 0.2 degrees or more, or the difference in humidity is 1% or more, a signal is transmitted to the temperature and humidity target signal generating device 24 indicating the correction required to Td or Tw and depending at the quantity and direction of the difference. When the measured temperature and humidity signals fulfill the standard condition of the prescribed rate of change, and, the difference from the preset target value is within the standard, the stability of the TG signal is evaluated.

Even when the temperature and humidity conditions in the periphery of the sample become stable, the TG signal does not always turn out to be stable. Depending especially on the property or the shape of the sample, the time required to reach humidity equilibrium for the sample and for the atmosphere differ. However, whether or not the humidity equilibrium is reached can be directly evaluated according to the stability of the physical property signal obtained by continuous measurement of the physical property of the sample. Namely, the stability of the TG signal can be evaluated whether or not the condition specifying the rate of change standard, for example, 0.01 mg per minute or under, is fulfilled. When this TG stable condition is fulfilled, a trigger signal to update the humidity target value in a stepwise manner is transmitted from the thermal stability determination circuit 22 to the temperature and humidity target signal generating device 24.

As a result, the target temperature of the constant temperature bath 1 is updated via the constant temperature bath temperature setting device 26. Accordingly, the temperature of the glass bottle 8 changes. Finally, the relative humidity of the atmosphere in the periphery of the sample changes, and the change is measured at the humidity measuring circuit 20 after passing through the humidity measuring sensor 19.

Thus, one step in a series of humidity control steps is completed. The same humidity scanning is repeated in a stepwise manner until the prescribed humidity control range is covered, after which the measurement will be completed.

In this embodiment, the humidity is controlled by introducing the saturated vapor corresponding to the wet bulb temperature into the sample chamber in which the temperature is controlled corresponding to the dry bulb temperature of the wet and dry bulb type hygrometer. Other apparatuses in which the desired relative humidity is obtained by mixing dry nitrogen and saturated vapor at a certain ratio are expensive because of their complicated structure and because they lack versatility since they cannot be used with a thermal analysis apparatus. However, a series of humidity control steps can be performed by changing the mixture ratio in a stepwise manner.

As for the different types of physical property signals, differential scanning calorimetry (DSC) signals, sample length (TMA) signals, and dynamic viscoelasticity signals, for example storage modulus or tangent delta signals, can be applied to the typical device used in the thermal analysis apparatus.

Figure 2:
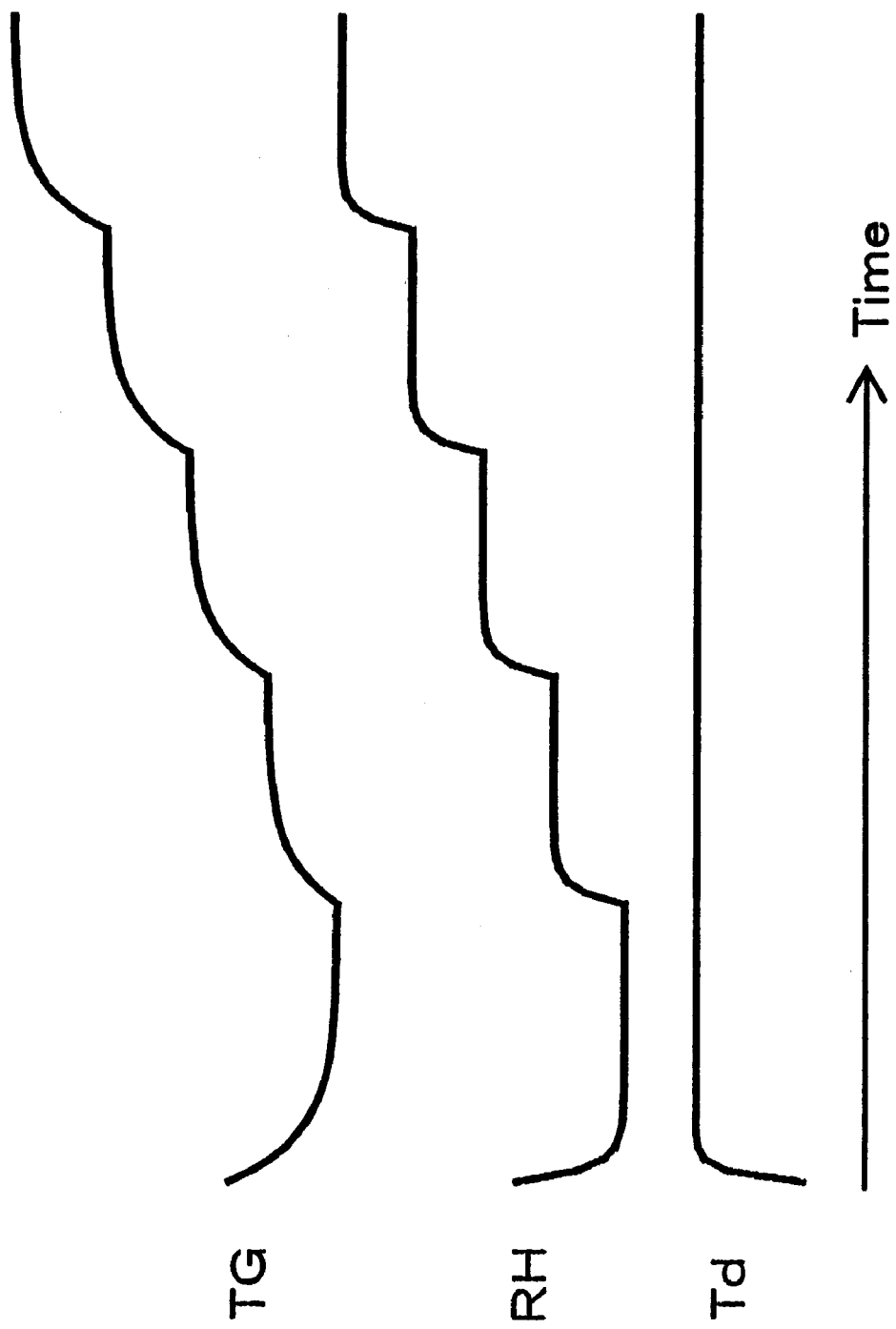
FIG. 2 is a schematic time chart of the signal obtained in the embodiment of the present invention.

FIG. 2 is a time chart schematically showing the time change of the thermogravimetry(TG) signal, relative humidity (RH) signal, and the temperature (Td) signal of the sample 1 during the performance of a series of humidity step control steps.

As mentioned above, according to the present invention, temperature and humidity of the sample are measured, and the difference from a set target value is continuously corrected. Thus the temperature and humidity conditions of the sample can be controlled as set by a target value, and humidity is scanned based on the stability of a physical property signal, which reflects changes in a physical property of the sample, in a stepwise manner without estimating the time required to reach humidity equilibrium in advance, which differs depending on properties or shape of the sample. Thus humidity dependency of a physical property of the sample can be accurately analyzed. Accordingly, the redundancy of the constant speed humidity scanning method usually requiring measurement data corresponding to the uncertain portion of the time required to reach the humidity equilibrium is eliminated. Therefore the analysis time can be kept to a minimum. Furthermore, the occurrence of error due to hysteresis in the constant speed humidity scanning method caused by the difference of the humidity scanning direction based on an underestimate of the humidity equilibrium time can be solved. Moreover, the apparatus of the present invention replaces the heating furnace of the thermal analysis apparatus with a simple humidity control system mainly comprising two constant temperature baths. This means it has high versatility and can be effectively used as a thermal analysis apparatus. The instrument is capable of automatic humidity step control measurement at low cost, and is suitable for evaluation of hygroscopicity, for example, chemicals.

Moreover, by controlling the humidity of the sample chamber, even in a situation where the sample has previously reached its equilibrium state at a certain humidity and temporarily deviates form its equilibrium, confirmation that it has returned to its equilibrium state by the measurement start can be performed with the trigger sinal. Therefore, evaluation of the temperature dependency of the changes in the weight of the sample and the thermal change can be started without deviating from its equilibrium state. Thus the thermal characteristics of a sample having a moisture content can be evaluated accurately.

What is claimed:

1. An automatic humidity step control thermal analysis apparatus comprising: a detector for detecting and measuring a physical property of a sample and for generating a physical property signal corresponding to the physical property of the sample; a sample chamber for housing the sample and which is capable of controlling the temperature and humidity of the sample housed in the sample chamber; a water chamber for generating water vapor at a preselected temperature and which is capable of controlling the temperature of water in the water chamber in a stepwise manner;

a heat insulating pipe for directing water vapor from the water chamber to the sample chamber; a signal stability determination circuit for receiving a physical property signal from the detector and for generating a trigger signal when a rate of change of the physical property signal drops below a preselected reference value; and control means for controlling the temperature of water in the water chamber in a stepwise manner in accordance with the trigger signal generated by the signal stability determination circuit to thereby adjust the humidity of the sample chamber in a stepwise manner.

2. An automatic humidity step control thermal analysis apparatus according to claim 1; wherein the physical property of the sample detected by the detector is the mass of the sample.

3. An automatic humidity step control thermal analysis apparatus according to claim 1; wherein the physical property of the sample detected by the detector is a difference in temperature between the sample and a reference material.

4. An automatic humidity step control thermal analysis apparatus according to claim 1; further comprising determining means for determining whether the sample has reached an equilibrium state at a preselected humidity in accordance with the trigger signal from the signal stability determination circuit; and wherein the control means includes means for changing the temperature of the sample housed in the sample chamber when the determining means determines that the sample has reached the equilibrium state and without causing the sample to deviate from the equilibrium state.

5. An automatic humidity step control thermal analysis apparatus according to claim 4; wherein the physical property of the sample detected by the detector is the mass of the sample.

6. An automatic humidity step control thermal analysis apparatus according to claim 4; wherein the physical property of the sample detected by the detector is a difference in temperature between the sample and a reference material.

7. An automatic humidity step control thermal analysis according to claim 1; wherein the control means comprises a temperature and humidity target signal generating device for generating a target humidity value of the sample chamber in accordance with the trigger signal from the signal stability determination circuit, and a constant temperature setting device for calculating a target temperature value in accordance with the target humidity value and for controlling the temperature of the water in the water chamber in accordance with the target temperature value.

8. An automatic humidity step control thermal analysis apparatus according to claim 7; wherein the signal stability determination circuit includes means for receiving the temperature and the humidity of the sample, measuring a shift in the temperature and in the humidity from the target temperature value and the target humidity value, respectively, and outputting correction signals for stabilizing the temperature and humidity of the sample.

9. An automatic humidity step control thermal analysis apparatus according to claims 1; wherein the sample chamber comprises a hollow heat-retaining furnace and a constant temperature circulator for circulating water around the heat-retaining furnace to set a temperature of the sample chamber.

10. An automatic humidity step control thermal analysis apparatus according to claim 9; wherein the heat-retaining furnace is generally cylindrical-shaped.

11. An automatic humidity step control thermal analysis apparatus according to claim 9; wherein the constant temperature circulator circulates the water around the heat-retaining furnace to set the temperature of the sample chamber in accordance with the trigger signal from the signal stability determination circuit.

12. An automatic humidity step control thermal analysis apparatus according to claim 1; further comprising heating means for heating the heat insulating pipe to prevent dew condensation.

13. An automatic humidity step control thermal analysis apparatus according to claim 12; wherein the heating means comprises a heater disposed in the heat insulating pipe.

14. An automatic humidity step control thermal analysis apparatus comprising:

a detector for detecting and measuring a physical property of a sample and for generating a physical property signal corresponding to the physical property of the sample;

a sample chamber for housing the sample;

a water chamber for generating water vapor;

a heat insulating pipe for directing water vapor from the water chamber to the sample chamber;

a signal stability determination circuit for receiving a physical property signal from the detector and for generating a trigger signal when a rate of change of the physical property signal drops below a preselected reference value; and control means for controlling a humidity of the sample chamber in a stepwise manner in accordance with the trigger signal generated by the signal stability determination circuit.

15. An automatic humidity step control thermal analysis according to claim 14; wherein the control means comprises a target signal generating device for generating a target humidity value of the sample chamber in accordance with the trigger signal from the signal stability determination circuit, and a constant temperature setting device for calculating a target temperature value in accordance with the target humidity value and for controlling the temperature of the water in the water chamber in accordance with the target temperature value.

16. An automatic humidity step control thermal analysis apparatus according to claim 15; wherein the signal stability determination circuit includes means for receiving a temperature and in a humidity of the sample, measuring a shift in the temperature and the humidity of the sample from the target temperature value and the target humidity value, respectively, and generating correction signals for stabilizing the temperature and humidity of the sample.

17. An automatic humidity step control thermal analysis apparatus according to claim 14; further comprising heating means heating the heat insulating pipe to prevent dew condensation.

18. An automatic humidity step control thermal analysis apparatus according to claim 17; wherein the heating means comprises a heater disposed in the heat insulating pipe.

19. An automatic humidity step control thermal analysis apparatus according to claim 14; wherein the physical property of the sample detected by the detector is the mass of the sample.

20. An automatic humidity step control thermal analysis apparatus according to claim 14; wherein the physical property of the sample detected by the detector is a difference in temperature between the sample and a reference material.

* * * * *